United States Patent
Di Maio

(10) Patent No.: US 11,576,926 B2
(45) Date of Patent: Feb. 14, 2023

(54) COMPOSITION FOR USE IN THE PREVENTION AND/OR TREATMENT OF EPISTAXIS

(71) Applicant: NEILOS S.R.L., Piano di Sorrento (IT)

(72) Inventor: Umberto Di Maio, Sant'Agnello (IT)

(73) Assignee: NEILOS S.R.L., Piano di Sorrento (IT)

( * ) Notice: Subject to any disclaimer, the term of this patent is extended or adjusted under 35 U.S.C. 154(b) by 0 days.

(21) Appl. No.: 17/275,762

(22) PCT Filed: Sep. 11, 2019

(86) PCT No.: PCT/IB2019/057652
§ 371 (c)(1),
(2) Date: Mar. 12, 2021

(87) PCT Pub. No.: WO2020/053783
PCT Pub. Date: Mar. 19, 2020

(65) Prior Publication Data
US 2022/0031732 A1 Feb. 3, 2022

(30) Foreign Application Priority Data
Sep. 12, 2018 (IT) .................. 102018000008524

(51) Int. Cl.
| | | |
|---|---|---|
| *A61K 9/00* | (2006.01) |
| *A61K 31/197* | (2006.01) |
| *A61K 31/355* | (2006.01) |
| *A61K 31/728* | (2006.01) |
| *A61K 31/19* | (2006.01) |
| *A61K 33/38* | (2006.01) |

(52) U.S. Cl.
CPC ............ *A61K 31/728* (2013.01); *A61K 31/19* (2013.01); *A61K 33/38* (2013.01); *A61K 31/355* (2013.01)

(58) Field of Classification Search
CPC .. A61K 9/0043; A61K 31/728; A61K 31/355; A61K 31/19; A61K 31/197; A61K 33/38; A61K 2300/00
USPC .......................................... 514/54
See application file for complete search history.

(56) References Cited

U.S. PATENT DOCUMENTS

2005/0164979 A1* 7/2005 Gross ...................... A61P 27/16
514/561

FOREIGN PATENT DOCUMENTS

| CN | 107661222 A | * | 2/2018 | |
| EP | 1094807 B1 | * | 4/2003 | ........... A61K 31/355 |

OTHER PUBLICATIONS

International Search Report and Written Opinion for corresponding PCT/IB2019/057652 dated Dec. 3, 2019, 11 Pages.

* cited by examiner

*Primary Examiner* — Ganapathy Krishnan
(74) *Attorney, Agent, or Firm* — Armstrong Teasdale LLP

(57) ABSTRACT

A synergistic composition of naturally occurring active ingredients is described, which has proved particularly effective in the treatment and/or prevention of epistaxis, particularly in acute or chronic episodes of infectious and inflammatory epistaxis. The composition includes the synergistic combination of hyaluronic acid or a salt thereof, silver, vitamin B5 or pro-vitamin B5, and optionally vitamin E or an ester thereof.

8 Claims, No Drawings

COMPOSITION FOR USE IN THE PREVENTION AND/OR TREATMENT OF EPISTAXIS

CROSS-REFERENCE TO RELATED APPLICATIONS

The present application is a National Stage application of International Patent Application No. PCT/IB2019/057652, filed Sep. 11, 2019, which claims the benefit of priority to Italian Patent Application No. 102018000008524, filed Sep. 12, 2018, each of which is hereby incorporated by reference herein in its entirety.

The present invention relates to a composition of substances preferably obtained from natural sources, which is effective in the prevention and/or treatment of epistaxis, particularly in the treatment and/or prevention of acute or chronic epistaxis phenomena due to infectious and inflammatory factors.

The term "epistaxis" refers to bleeding from the nasal passages. It can also be defined as a haemorrhage from the nose or neighbouring anatomical regions (for example paranasal sinuses, cavernous sinus, skull base, pterygomaxillary fossa, rhinopharynx) caused by vascular erosion or rupture, which appears as a bleeding from the nostrils or a blood drain at the back into the nasopharynx. Depending on the site of onset, two types of epistaxis can be distinguished:

1) anterior epistaxis, which occurs at the front of the nasal septum, in an area called locus Valsalvae. The blood reaches this area from the external carotid artery, through the superior labial branch of the facial artery and the terminal branches of the sphenopalatine artery and finally from the internal carotid artery through the anterior and posterior ethmoidal arteries.

2) posterior epistaxis, which most typically originates from the region of the sphenopalatine artery and its branches.

The two types of epistaxis can coexist and in this case it is referred to as anterior-posterior epistaxis.

Anterior epistaxis originates from a more easily accessible location, therefore it is easier to recognize and treat, and less dangerous. Posterior epistaxis is more difficult to detect and treat, and since the blood is often swallowed, it can cause substantial blood loss before a subject becomes aware of it.

Epistaxis can also be classified according to the vascular origin. However, the distinction between arterial haemorrhage and venous haemorrhage can be difficult, and in any case it is based on the detection of a more or less high haemorrhagic pressure at the bleeding point and on the colour of the blood. As regards the hypothetical origin of bleeding from tributary branches of the internal or external carotid system, the presumable anatomical site of origin can be referred to, most probably the external carotid artery in the case of posterior bleeding, and vice versa, the internal carotid artery in case of upper bleeding from the ethmoidal arteries. It should however be pointed out that many potentially haemorrhagic nasal areas (such as for example the anterior septal area) are tributaries of both carotid systems.

The course and mode of manifestation may also vary, and several conditions can be distinguished, both in terms of time and as regards the type and site of bleeding. The extent of haemorrhage during each individual episode or in the context of repeated episodes may represent clinical pictures of varying severity, which may occur as rapid resolution sporadic episodes or as abundant blood loss, which can lead to conditions that are sometimes life-threatening to patients.

Epistaxis can be further distinguished, based on the cause, into essential epistaxis, that is due to nasal disease, or symptomatic epistaxis, due to other kinds of causes.

Local factors that can generate essential epistaxis are:
inflammatory and infectious: rhinitis, (allergic, bacterial or viral) sinusitis, nasal polyposis;
environmental: hot and dry air, breathing of pure oxygen through the nose, abnormalities of anatomical structures, atrophic rhinitis;
traumatic: fracture of the nasal bones, rubbing caused by "fingers in the nose", the presence of a nasogastric tube, nasal-tracheal intubation manoeuvres during anaesthesia, head trauma;
foreign bodies in the nose, the presence of parasites in the nose, perforations of the nasal septum, the action of various chemical substances (cocaine, excessive use of spray vasoconstrictor drugs for decongestant purposes, ammonia, and so on);
vascular (for example, carotid, extradural or cavernous sinus aneurysms) and neoplastic (for example, juvenile nasopharyngeal angiofibroma, squamous carcinoma).

Causes of symptomatic epistaxis include:
vascular events such as hypertension, arteriosclerosis and Rendu-Osler disease or "hereditary haemorrhagic telangiectasia", characterized by structural disruption of the vessel wall and vascular dilatations, which give rise to formations of the angiomatous type;
inflammatory and infectious factors such as tuberculosis, syphilis, systemic lupus erythematosus;
coagulation problems, such as hypovitaminosis K, anticoagulant therapies, thrombocytopenia, haemophilia;
other causes, such as kidney and liver disease, alcoholism, metabolic and connective tissue diseases.

In most patients with epistaxis, a conservative treatment is sufficient, which is carried out by pinching the tip of the nose for 15 minutes or less, or by topical application of vasoconstrictors and moisturizing creams. In cases that do not respond to conservative treatment, cauterization (with chemicals such as silver nitrate in minor bleeding or electrical cauterization with specialized equipment in cases of more serious bleeding) or tamponade with various materials is carried out. Very severe cases may require posterior tamponade, surgery or embolization.

The availability of a product based on natural substances and effective in the treatment and/or prevention of epistaxis, which makes it possible to avoid the aforementioned conventional treatments, which in many cases are painful or in any case inconvenient for the patient, would be extremely useful and advantageous.

These and other needs are met by the present invention, which provides a composition characterised in that it comprises a synergistic combination of active ingredients obtained from natural sources, the aforesaid combination having proved particularly effective against epistaxis, particularly infective or inflammatory epistaxis.

The composition of the invention is as defined in appended claim 1. Further features and advantages of the invention are defined in the dependent claims. The claims form an integral part of the present specification.

A detailed description of some preferred embodiments of the invention is provided hereinafter.

The synergistic composition of the present invention is useful for the treatment and prevention of epistaxis.

In the composition of the present invention the synergistic action takes place between hyaluronic acid or a salt thereof, silver, vitamin B5 or pro-vitamin B5, and optionally vitamin E or an ester thereof.

Hyaluronic acid (HA) is a naturally occurring polyanionic polymer. It is a large, negatively charged linear polymer consisting of repeating disaccharide units of D-glucuronic acid and N-acetyl-D-glucosamine alternately linked to each other by β-1,4 and β-1,3 glycosidic bonds. Hyaluronic acid is the main component of the extracellular matrix (ECM), it belongs to the family of glycosaminoglycans (GAG) and is a molecule of varying size. Inside our body it is distributed in the form of salt and in high concentrations mainly in the connective tissue, skin, umbilical cord, synovial fluid, vitreous humour, but also in the lungs, kidneys, brain and muscles.

It has been shown that the length of the HA chains plays an important biological role, because the molecular weight of hyaluronic acid implies different effects on cellular behaviour. In fact, enzymes that are able to break the large hyaluronic acid molecules by hydrolysing the β1-4 bonds between the N-acetyl-D-glucosamine and D-glucuronic acid residues are physiologically present in the body. These enzymes are called hyaluronidases, β-D-glucuronidases and β-N-acetylhexosaminidases.

The HA produced has a physiological turnover of 10-100 mg/day in adults. It is mainly metabolised by the liver endothelial cells and cleared by the kidneys. It performs its function by covalently binding to a variety of proteins, called hyaladherins, affecting the function thereof. These proteins are referred to as binding proteins and include, a.o., the CD44, RHAMM, TNFIP6, Brevican, SHAP, and LYVE1 receptors. Some of these are found in the extracellular matrix (ECM), some bound to cell membranes.

Among the skin and connective tissue components, hyaluronic acid plays a key role in the pathophysiological, clinical and therapeutic fields. In fact, it has a wide range of applications thanks to excellent physicochemical properties such as biodegradability, biocompatibility, non-toxicity and non-immunogenicity. Its multiple functions, as well as its consistency and its biocompatibility, therefore, give the possibility of finding numerous clinical applications for it, including synovial fluid supplementation in case of arthritis, tissue regeneration promotion in surgical wounds in eye surgery, as a filler for wrinkles in the aesthetic field, and for the treatment of lung diseases, asthmatic forms and fibrosis.

Among the various uses of hyaluronic acid, it was noted that all the problems for which it was used had in common the presence of tissue damage in which the gene expression of the HAS enzyme involved in the formation of hyaluronic acid was increased. This tissue damage is repaired thanks to HA's ability to bind water to the tissues, thus forming a hydrogel film that supports dermal regeneration and growth. These cross-linked HA hydrogel films accelerate the healing of full-thickness wounds, presumably by providing a highly hydrated and non-immunogenic environment that promotes tissue repair. Since HA is highly hydrophilic, it is a polymer that is well suited to applications that require minimal cell adhesion. Postoperative adhesions, which form between adjacent tissue layers after surgery, prevent wound healing and often require additional surgery to be repaired successfully. The barriers made by cross-linked HA have been used effectively to prevent the formation of such adhesions. Furthermore, adhesion of bacteria to biomaterials can cause infections and pose a great risk to the patient; taking this into account, HA has also been used to prevent bacterial adhesion to dental implants, intraocular lenses and catheters.

In the context of the present invention, hyaluronic acid is of considerable interest thanks to its dual action as a moisturizer and a barrier. In fact, in cases of chronic epistaxis, regardless of the causes that generated it, the mucous membranes of the nasal cavities are known to be continuously exposed to oxidative and inflammatory phenomena, dryness, burning, itching, and poor hydration.

Normally the skin has its own defence systems against both endogenous and exogenous insults, for example it has antioxidant activity, its own tissue remodelling capacity, as well as lubrication action in response to dryness phenomena. However, when the insult is chronic and occurs continuously, the soothing, defensive and regenerative capacities of the skin and mucous membranes begin to fail. In these cases, more than ever it is necessary that the skin remain hydrated, be stimulated to regenerate, and be protected from the onset of inflammatory and/or infectious states.

In a preclinical study, the ability of hyaluronic acid to regenerate the epithelium of the stratum corneum was assessed in rat models. A solution containing 0.3% HA was statistically significant in enhancing re-epithelialization of corneal wounds in rat models with type 1 diabetes.

In a Swiss randomized clinical trial the effectiveness of a hyaluronic acid-containing cream (15 g cream tube, 1 g of cream contains 2 mg of HA) was assessed in comparison to ointments based on plant extracts, and the healing potential of the nasal mucosa after surgery in the nasal cavity was assessed in 56 patients. After a 6-week treatment, the group treated with hyaluronic acid was shown to recover faster and more effectively than the ointment group. Furthermore, hyaluronic acid prevented excessive formation of bloody scabs already after the first week of treatment. The treatment was well tolerated by all trial participants, who were also highly compliant for the HA-based cream. No adverse effects were reported during the trial.

Silver is a transition metal represented by the symbol Ag in the periodic table.

The products on the market contain different forms of silver, such as silver proteinate, in which silver atoms are attached to protein molecules that act as carriers, or colloidal silver in the ionic form obtained by electrolysis of at least 99.9% pure silver bars. Other products contain silver in the elemental form, such as micronized silver, complexed silver citrate, silver sulfadiazine, or in the form of specific silver complexes such as silicon dioxide functionalized with silver ions and chlorhexidine (SCX), or titanium dioxide complexed with silver ions and benzalkonium chloride (TIAB), silicon dioxide complexed with silver ions and benzalkonium chloride (SIAB).

All the aforementioned forms of silver are suitable for use in the context of the present invention.

Known medical uses of silver include its incorporation into wound gauzes, creams and as a germicidal coating in medical devices; it is also used as an ear antiseptic, an antiseptic for topical use, and a nasal decongestant.

Whatever the form of silver inside a product, the bacteriostatic and bactericidal effect is caused by the silver ($Ag^+$) ion, which is biologically active and endowed with a broad-spectrum activity due to its ability to interfere with the normal bacterial metabolic processes, in particular with those involving the use of oxygen, thus increasing the oxidative level of the cell and thereby causing its death.

In fact, its activity as an antibiotic affects about 650 gram-positive and gram-negative microorganisms, viruses and parasites. More particularly, the mechanisms of action of silver are different and attributable to at least four types of biochemical interactions, namely: interactions with the bacterial cell membrane leading to impairment of its activity, formation of complexes with components of the respiratory chain leading to their inactivation, formation of complexes with bacterial DNA and RNA with replication and protein synthesis inability, and chemical reactivity with sulfhydryl end groups of enzymatic and structural proteins.

All these actions effectively kill microorganisms. Since human cells are larger and more evolved and have their respiratory chain confined to the mitochondria and not to the outer membrane, they do not undergo the bacteriostatic and bactericidal effects of silver ions.

In addition to the antibacterial effect, silver is also used for nasal decongestion, although the decongestant mechanism of action is still not entirely clear. It is hypothesized to cause precipitation of serum exudate proteins, with reduction of the associated edema.

In the context of the present invention, silver is of considerable interest thanks to its dual decongestant and antibacterial action on the nasal mucosa. In patients with chronic epistaxis, because of the continuous inflammatory processes due to bleeding and rubbing, the nasal mucosa is congested by edema formation and exudate accumulation, and this condition favours the development of microbial infections. The dual decongestant and antibacterial action simultaneously ensures reduction of edema and swelling and protection from pathogen proliferation.

The antibacterial capacity of silver ions against *Escherichia coli* and *Staphylococcus aureus*, the main culprits of bovine infections (mastitis), was assessed in a preclinical study. The results of this study confirmed the high affinity of silver for some of the proteins essential for these bacteria, inducing therein structural changes such as increased permeability, impairment of normal mechanisms of ion transport through the plasma membrane, eventually leading to death.

The use of silver was also assessed in a clinical trial in 90 patients with non-allergic and idiopathic rhinitis. The symptomatology, the biopsy results and the physical state of the nasal cavities were assessed as parameters of improvement. In patients who received the therapy, an improvement in the rhinorrhea and the nasal decongestion was found in 93% and 80% of cases, respectively. An improvement in the condition of the nasal epithelium was also detected in over 70% of patients. Treatment with silver was statistically significant compared to placebo.

The antibacterial activity of a solution containing colloidal silver (0.015 mg/mL solution, twice daily) was assessed in a clinical trial conducted in Australia in patients with CRS (chronic rhinosinusitis). The results of this study showed that after 10 days of treatment, silver performs an antibacterial action comparable to that of oral antibiotics, demonstrating a good profile in terms of efficacy and safety.

Pantothenic acid is produced by both plants and microorganisms, but higher animals and humans must include it in the diet. Pantothenic acid is essential for normal epithelial function and is a component of coenzyme A, which acts as a cofactor for a variety of enzyme-catalyzed reactions, which are important in the metabolism of carbohydrates, fatty acids, proteins, gluconeogenesis, sterols, steroid hormones and porphyrins.

Dexpanthenol (the D form of pantothenol) is the alcohol obtained from pantothenic acid. It is also known as provitamin B5, and is the most stable form of vitamin B5, therefore it is widely used in the pharmaceutical and cosmetic sector. Thanks to its excellent skin hydration capacity and anti-inflammatory effects, dexpanthenol enhances skin moisture by penetrating the deeper layers of the skin and moisturizing it thoroughly. Furthermore, the use of dexpanthenol was shown to activate fibroblast proliferation, both in vitro and in vivo. Accelerated re-epithelialization was also observed in wound healing, which was monitored by transepidermal water loss as an indicator of an intact epidermal barrier function.

In addition, dexpanthenol was shown to have an anti-inflammatory effect on experimental ultraviolet-induced erythema. Stimulation of epithelialization, granulation and mitigation of pruritus are the most important effects of formulations containing dexpanthenol. Dexpanthenol was assessed for its effectiveness in improving wound healing in double-blind placebo clinical trials. Epidermal wounds treated with dexpanthenol emulsion showed a reduction in erythema and more elastic and solid tissue regeneration. Monitoring of transepidermal water loss showed a significant acceleration of epidermal regeneration as a result of dexpanthenol therapy, as compared to placebo.

In the context of the present invention, dexpanthenol is of considerable interest thanks to its ability to penetrate deeply into the nasal mucosa and promote its regeneration. Furthermore, it exerts a moisturizing action on the mucous membranes and dry nasal crusts and a soothing action on the reddened and inflamed skin of the nostrils.

The regeneration capacity of dexpanthenol cream on epithelial tissue was assessed in a preclinical study in mouse models. The regeneration rate of the dexpanthenol-treated group was statistically higher than the control group after 20 days.

The capacity of a medical device (20 ml spray) with 5% dexpanthenol was assessed in a clinical trial for the treatment of dry rhinitis compared to placebo. The result confirmed the clinical relevance and statistical significance of dexpanthenol compared to placebo, the former improving the symptoms of rhinitis, especially as regards the formation of scabs and the improvement of the respiratory capacity at the nasal level.

Furthermore, the improvement of the symptomatology of "rhinitis sicca syndrome" (dry nasal mucous membranes, burning, itching, scabs, sensation of nasal obstruction, epistaxis and cacosmia) was assessed in a 2014 German observational study. The symptomatic reduction brought about by a nasal spray based on 0.5% ectoin (amino acid produced by bacteria) and by a nasal spray based on ectoin and dexpanthenol (0.5% ectoin and 1.0% dexpanthenol) was assessed and the results obtained were compared. The patients enrolled were 50 for ectoin and 30 for ectoin plus dexpanthenol. Although nasal obstruction, rhinorrhea and crusting decreased significantly with both treatments, the spray comprising dexpanthenol also resulted in a significant reduction in recurrent nose bleeding, pharyngitis, exudate viscosity during inflammatory phenomena and cacosmia, whereas this did not occur with ectoin alone. In conclusion, dexpanthenol has been shown to bring a plus to rhinitis sicca symptoms, particularly by reducing recurrent bleeding (epistaxis).

Vitamin E, or tocopherol, is a group of fat-soluble vitamins (alpha, beta, gamma and delta-tocopherol and alpha, beta, gamma and delta-tocotrienol). Vitamin E is found in many vegetables, for example in fruit, hemp oil, olive oil, and above all in wheat germ oil. The main role of vitamin E is to protect the body's tissues from peroxidation reactions and free radicals. It is therefore able to prevent the oxidation of polyunsaturated fatty acids, an event responsible for lipid peroxidation triggered by free radicals through chain reactions which carry on the process. Vitamin E is able to block this process by donating a hydrogen atom to lipid peroxyl radicals, making them less reactive and thus blocking peroxidation. This redox reaction transforms vitamin E into an α-tocopheroxyl radical, which is able to react with vitamin C, coenzyme Q10 or glutathione, reforming alpha-tocopherol. Thanks to its antioxidant activity, vitamin E is also able to regulate the production of mediators of the arachidonic acid cascade. Arachidonic acid is released from membrane phospholipids following the action of phospholipase A2, an enzyme activated by lipid peroxides, whose formation is reduced by vitamin E, which is therefore also capable of modulating the activity of lipoxygenase and cyclooxygenase. Therefore, vitamin E is associated with reduced production of prostaglandin E2 (PGE2). Since PGE2 inhibits lymphocyte proliferation and NK cell activity, this could be one of the immunomodulatory mechanisms of vitamin E. The antioxidant action of vitamin E allows the cells to be protected from free radicals and therefore premature ageing. Furthermore, vitamin E supports the immune system defences, improves oxygenation, prevents heart disease by regulating cholesterol levels and protecting the artery walls from oxidation.

A study carried out in mice showed that topical application of vitamin E exerts a remarkable antioxidant and anti-inflammatory action. A double application of the TPA agent (12-O-tetradecanoylphorbol-13-acetate) induces a massive inflammatory response accompanied by oxidative stress. The application of vitamin E administered 30 minutes before TPA produces an anti-inflammatory and antioxidant action, as it inhibits the release of hydrogen peroxide, the activity of the myeloperoxidase (MPO) and xanthine oxidase (XO) enzymes, and lipid peroxidation (LPO). Furthermore, a clinical trial carried out on 112 patients with seasonal allergic rhinitis showed that treatment with 800 mg/day of vitamin E in addition to the classic anti-allergy treatment resulted in a reduction of the nasal symptoms associated with allergic rhinitis, which is a factor that often causes repeated epistaxis.

As indicated above, the composition of the present invention is effective in the treatment and/or prevention of epistaxis. The present invention allows an antibacterial effect, an antioxidant effect, a moisturizing effect and an anti-inflammatory effect to be obtained simultaneously.

The present invention represents a valid and quick intervention to mitigate the inflammatory symptoms following epistaxis, such as crusting, dryness of the nasal cavities, burning, itching, and poor hydration of the mucous membranes. Hyaluronic acid helps to keep the nasal mucosa well hydrated, softens the bloody crusts allowing a quick and less painful healing thereof. Silver has a bacteriostatic effect in the nasal cavity by interfering with the replication mechanisms of the bacteria colonizing the mucous membranes. Dexpanthenol is highly effective due to its ability to penetrate deeply into the nasal mucosa and promote its regeneration. Furthermore, it exerts a moisturizing action on the mucous membranes and dry nasal crusts and a soothing action on the reddened and inflamed skin of the nostrils. Vitamin E counteracts the formation of free radicals resulting from the numerous inflammatory and haemorrhagic episodes typical of epistaxis.

Moreover, the present inventors found that hyaluronic acid or a salt thereof, vitamin B5 or pro-vitamin B5, and silver ions, when used in combination, advantageously exhibit a synergistic action.

In a preferred embodiment, the composition of the present invention is prepared as a pharmaceutical dosage form comprising from 0.05 to 5500 mg of hyaluronic acid or a salt thereof; from 0.0001 to 6000 mg of silver, understood as ionic silver or salified or complexed silver; from 0.1 to 7000 mg of vitamin B5 or pro-vitamin B5; and, optionally, from 0.01 to 10000 mg of vitamin E, in addition to the usual excipients used in the preparation of the selected dosage form.

Additional preferred amounts of the active ingredients are:

Hyaluronic acid or a salt thereof: from 0.05 mg to 1 mg: from 1 mg to 10 mg: from 10 mg to 20 mg; from 20 to 30 mg; from 30 mg to 40 mg; from 40 mg to 50 mg: from 50 mg to 60 mg: from 60 mg to 70 mg; from 80 mg to 90 mg: from 90 mg to 100 mg; from 100 mg to 150 mg; from 150 mg to 200 mg; from 200 mg to 300 mg; from 300 mg to 400 mg; from 400 mg to 500 mg; from 500 mg to 600 mg; from 600 mg to 700 mg: from 700 mg to 800 mg: from 800 mg to 900 mg; from 1000 mg to 1100 mg, from 1100 mg to 1200 mg; from 1200 mg to 1300 mg: from 1300 mg to 1400 mg; from 1400 mg to 1500 mg; from 1500 mg to 2000 mg: from 2000 mg to 2500 mg; from 2500 mg to 3000 mg: from 3000 mg to 3500 mg; from 3500 mg to 4000 mg; from 4000 mg to 4500 mg: from 4500 mg to 5000 mg; from 5000 mg to 5500 mg;

Silver, understood as ionic silver or salified or complexed silver: from 0.0001 mg to 0.001 mg; from 0.001 mg to 0.1 mg; from 0.1 mg to 1 mg; from 1 mg to 10 mg; from 10 mg to 20 mg; from 20 to 30 mg: from 30 mg to 40 mg; from 40 mg to 50 mg: from 50 mg to 60 mg: from 60 mg to 70 mg: from 80 mg to 90 mg: from 90 mg to 100 mg: from 100 mg to 150 mg: from 150 mg to 200 mg; from 200 mg to 300 mg; from 300 mg to 400 mg; from 400 mg to 500 mg; from 500 mg to 600 mg; from 600 mg to 700 mg; from 700 mg to 800 mg: from 800 mg to 900 mg; from 1000 mg to 1100 mg, from 1100 mg to 1200 mg; from 1200 mg to 1300 mg: from 1300 mg to 1400 mg; from 1400 mg to 1500 mg; from 1500 mg to 2000 mg; from 2000 mg to 2500 mg; from 2500 mg to 3000 mg; from 3000 mg to 3500 mg; from 3500 mg to 4000 mg; from 4000 mg to 4500 mg; from 4500 mg to 5000 mg; from 5000 mg to 5500 mg; from 5500 mg to 6000 mg;

Vitamin B5 or pro-vitamin B5: from 0.1 to 1 mg; from 1 mg to 10 mg; from 10 mg to 20 mg; from 20 to 30 mg; from 30 mg to 40 mg; from 40 mg to 50 mg; from 50 mg to 60 mg; from 60 mg to 70 mg; from 80 mg to 90 ng; from 90 mg to 100 mg; from 100 mg to 150 mg; from 150 mg to 200 mg; from 200 mg to 300 mg; from 300 mg to 400 mg; from 400 mg to 500 mg; from 500 mg to 600 mg; from 600 mg to 700 mg; from 700 mg to 800 mg; from 800 mg to 900 mg: from 1000 mg to 1100 mg, from 1100 mg to 1200 mg; from 1200 mg to 1300 mg; from 1300 mg to 1400 mg; from 1400 mg to 1500 mg; from 1500 mg to 2000 mg; from 2000 mg to 2500 mg; from 2500 mg to 3000 mg; from 3000 mg to 3500 mg; from 3500 mg to 4000 mg; from 4000 mg to 4500 mg; from 4500 mg to 5000 mg; from 5000 mg to 5500 mg; from 5500 mg to 6000 mg; from 6000 mg to 6500 mg; from 6500 mg to 7000 mg; and optionally Vitamin E: from 0.01 to 0.1 mg; from 0.1 to 1 mg; from 1 mg to 10 mg; from 10 mg to 20 mg; from 20 to 30 mg; from 30 mg to 40 mg; from 40 mg to 50 mg; from 50 mg to 60 mg; from 60 mg to 70 ng; from 80 mg to 90 mg; from 90 mg to 100 mg; from 100 mg to 150 mg; from 150 mg to 200 mg; from 200 mg to 300 mg; from 300 mg to 400 mg; from 400 mg to 500 mg; from 500 mg to 600 mg; from 600 mg to 700 mg; from 700 mg to 800 mg; from 800 mg to 900 mg; from 1000 mg to 1100 mg, from 1100 mg to 1200 mg; from 1200 mg to 1300 mg; from 1300 mg to 1400 mg; from 1400 mg to 1500 mg; from 1500 mg to 2000 mg; from 2000 mg to 2500 mg; from 2500 mg to 3000 mg; from 3000 mg to 3500 mg; from 3500 mg to 4000 mg; from 4000 mg to 4500 mg; from 4500 mg to 5000 mg; from 5000 mg to 5500 mg; from 5500 mg to 6000 mg; from 6000 mg to 6500 mg; from 6500 mg to 7000 mg; from 7000 mg to 7500 mg; from 7500 mg to 8000 mg; from 8000 mg to 8500 mg; from 8500 mg to 9000 mg; from 9000 mg to 9500 mg; from 9500 mg to 10000 mg.

In a further preferred embodiment, the composition of the present invention is prepared as a pharmaceutical dosage form comprising:
from 0.01 to 50 wt % of hyaluronic acid or a salt thereof, preferably in an amount ranging from 0.1% to 20%;
from 0.0001 to 20 wt % of silver, understood as ionic or salified or complexed silver, preferably in an amount ranging from 0.001% to 10%;
from 0.1 to 50 wt % of vitamin B5 or pro-vitamin B5, preferably in an amount ranging from 0.5% to 20%;
and optionally from 0.01% to 50 wt % of vitamin E, preferably in an amount ranging from 0.1% to 20%, in addition to the usual excipients used in the preparation of the selected dosage form. The percentages by weight indicated above refer to the total weight of the composition including the excipients.

Further preferred concentrations of the active ingredients in the pharmaceutical dosage form are:
Hyaluronic acid or a salt thereof: from 0.1% to 0.2%; from 0.2% to 0.3%; from 0.3% to 0.4%; from 0.4% to 0.5%; from 0.5% to 0.6%; from 0.6% to 0.7%; from 0.7% to 0.8%; from 0.8% to 0.9%; from 0.9% to 1%; from 1% to 2%; from 2% to 3%; from 3% to 4%; from 4% to 5%; from 5% to 6%; from 6% to 7%; from 7% to 8%; from 8% to 9%; from 9% to 10%;
Silver (understood as ionic silver or salified silver or complexed silver): from 0.001% to 0.005%; from 0.005% to 0.01%; from 0.01% to 0.05%; from 0.05% to 0.10%; from 0.1% to 0.2%; from 0.2% to 0.3%; from 0.3% to 0.4%; from 0.4% to 0.5%; from 0.5% to 0.6%; from 0.6% to 0.7%; from 0.7% to 0.8%; from 0.8% to 0.9%; from 0.9% to 1%; from 1% to 2%; from 2% to 3%; from 3% to 4%; from 4% to 5%; from 5% to 6%; from 6% to 7%; from 7% to 8%; from 8% to 9%; from 9% to 10%;
Vitamin B5 or pro-vitamin B5: from 0.5% to 0.6%; from 0.6% to 0.7%; from 0.7% to 0.8%; from 0.8% to 0.9%; from 0.9% to 1%; from 1% to 2%; from 2% to 3%; from 3% to 4%; from 4% to 5%; from 5% to 6%; from 6% to 7%; from 7% to 8%; from 8% to 9%; from 9% to 10%; from 10% to 11%; from 11% to 12%; from 12% to 13%; from 13% to 14%; from 14% to 15%; from 15% to 16%; from 16% to 17%; from 17% to 18%; from 18% to 19%; from 19% to 20%; and optionally
Vitamin E: from 0.1% to 0.2%; from 0.2% to 0.3%; from 0.3% to 0.4%; from 0.4% to 0.5%; from 0.5% to 0.6%; from 0.6% to 0.7%; from 0.7% to 0.8%; from 0.8% to 0.9%; from 0.9% to 1%; from 1% to 2%; from 2% to 3%; from 3% to 4%; from 4% to 5%; from 5% to 6%; from 6% to 7%; from 7% to 8%; from 8% to 9%; from 9% to 10%; from 10% to 11%; from 11% to 12%; from 12% to 13%; from 13% to 14%; from 14% to 15%; from 15% to 16%; from 16% to 17%; from 17% to 18%; from 18% to 19%; from 19% to 20%.

The percentages by weight indicated above refer to the total weight of the composition including the excipients.

The preferred route of administration of the composition of the present invention is by topical application. The preferred pharmaceutical dosage forms for this purpose are nasal drops, nasal cream, nasal ointment, nasal spray, nasal gel and nasal gauze.

The following examples are provided for illustration purposes only and are not intended to limit the scope of the invention as defined in the appended claims.

EXAMPLES

EXAMPLE 1

| Active ingredient | Amount based on the total weight of the composition |
| --- | --- |
| Hyaluronic acid | 0.15% |
| Silver | 0.005% |
| Dexpanthenol | 1% |
| Vitamin E | 2% |

Pharmaceutical form: nasal drops

EXAMPLE 2

| Active ingredient | Amount based on the total weight of the composition |
| --- | --- |
| Hyaluronic acid | 0.2% |
| Silver | 0.0006% |
| Dexpanthenol | 5% |
| Vitamin E | 2% |

Pharmaceutical form: nasal cream

EXAMPLE 3

| Active ingredient | Amount based on the total weight of the composition |
| --- | --- |
| Hyaluronic acid | 0.2% |
| Silver | 1.5% |
| Dexpanthenol | 2.5% |
| Vitamin E | 1.5% |

Pharmaceutical form: nasal spray

EXAMPLE 4

| Active ingredient | Amount based on the total weight of the composition |
| --- | --- |
| Hyaluronic acid | 0.3% |
| Silver | 2% |
| Dexpanthenol | 5% |
| Vitamin E | 2.5% |

Pharmaceutical form: nasal gel

EXAMPLE 5

| Active ingredient | Amount based on the total weight of the composition |
| --- | --- |
| Hyaluronic acid | 0.5% |
| Silver | 2% |
| Dexpanthenol | 5% |
| Vitamin E | 2% |

Pharmaceutical form: nasal gauze

Efficacy Testing

The efficacy of the composition object of the present invention has been assessed according to experimental protocols known to those skilled in the art. In particular, in vitro and/or in vivo assays known in the scientific literature can be used for assessing the different actions of the composition according to the present invention.

In vitro assays, such as, for example, the measurement of the TEWL (Trans-Epidermal Water Loss), are suitable to demonstrate the moisturizing effect of the composition according to the present invention. TEWL is an indicator of the efficiency of the skin barrier function and its measurement provides an indication of the resistance offered by the stratum corneum to the passage of water from the inside to the outside, and vice versa.

In vitro assays, such as, for example, the DPPH test, the radical scavenging activity on nitric oxide or on the peroxynitrile radical, the TEAC (total radical-trapping antioxidant parameter), FRAP (ferric reducing-antioxidant power), HORAC (hydroxyl radical averting capacity), ORAC (oxygen radical absorbance capacity) tests, and the like, are suitable to demonstrate the antioxidant efficacy of the composition according to the present invention.

In vitro assays, such as, for example, broth dilution (the sensitivity of the microorganism is estimated based on whether it grows or not in a culture medium at different concentrations of the sample) and agar diffusion (where a standardized concentration of the sample is applied in a broth culture of bacteria and the diffusivity of the sample within the medium is calculated), are suitable to demonstrate the antibacterial efficacy of the composition according to the present invention.

In vitro assays which assess the ability to inhibit the release of inflammatory cytokines such as IL-1, IL-6 and TNF-$\alpha$ and to inhibit the expression of enzymes such as COX-2 and IL-1$\beta$-induced metalloprotease-13 in primary human cell cultures (e.g. macrophages, chondrocytes, and fibroblasts), are suitable to demonstrate the anti-inflammatory efficacy of the composition according to the present invention.

According to an in vivo model, the composition is tested for its haemostatic effect on different types of animals. The animals are sedated by administering appropriate agents (such as, for example, ketamine, lidocaine) by injection. Then, the wounds are reproduced on the front, right and left sides of the nasal septum by applying a light pressure with surgical forceps, thus causing bleeding. The wounds are then treated on one side with the individual components of the composition or with a combination thereof (the object of the present invention), and on the other side of the nasal septum with saline until bleeding stops. The estimated parameter will therefore be the duration of the bleeding, which is significantly shorter in the case of treatment with the composition object of the present invention, compared to the application of the individual components and to saline.

The invention claimed is:

1. A method of treating epistaxis in a subject in need thereof, comprising administering to the subject a pharmaceutically effective amount of a composition comprising hyaluronic acid or a salt thereof, silver, vitamin B5 or pro-vitamin B5, and vitamin E or an ester thereof, wherein treating epistaxis includes hemostasis.

2. The method according to claim 1, wherein the silver is in the form of colloidal silver, silver proteinate, elementary silver, micronized silver, silver salts, or silver complexed with other ingredients.

3. The method according to claim 1, wherein the composition is a pharmaceutical dosage form for topical application.

4. The method according to claim 3, wherein the pharmaceutical dosage form comprises from 0.05 to 5,500 mg of hyaluronic acid or a salt thereof, from 0.0001 to 6,000 mg of silver, including one of ionic or salified or complexed silver, from 0.1 to 7,000 mg of vitamin B5 or pro-vitamin B5, and optionally from 0.01 to 10,000 mg of vitamin E or an ester thereof.

5. The method according to claim 3, wherein the pharmaceutical dosage form comprises from 0.01 to 50 wt % of hyaluronic acid or a salt thereof, from 0.0001 to 20 wt % of silver including one of ionic or salified or complexed silver, from 0.1 to 50 wt % of vitamin B5 or pro-vitamin B5, and optionally from 0.01% to 50 wt % of vitamin E or an ester thereof.

6. The method according to claim 3, wherein the pharmaceutical dosage form for topical application is selected from the group consisting of nasal drops, nasal cream, nasal ointment, nasal spray, nasal gel, and nasal gauze.

7. The method according to claim 1, wherein the epistaxis is infectious or inflammatory in nature.

8. The method according to claim 1, wherein the composition is administered topically.

* * * * *